US006635178B2

(12) United States Patent
Bowman et al.

(10) Patent No.: US 6,635,178 B2
(45) Date of Patent: Oct. 21, 2003

(54) PATHOGEN INACTIVATION IN BIOSOLIDS WITH CAVITATION

(76) Inventors: Dwight D. Bowman, 396 Coddington Rd., Ithaca, NY (US) 14850; Elizabeth A. Fogarty, 27 Connecticut Hill Rd. #1, Newfield, NY (US) 14867

( * ) Notice: Subject to any disclaimer, the term of this patent is extended or adjusted under 35 U.S.C. 154(b) by 0 days.

(21) Appl. No.: 10/015,028

(22) Filed: Dec. 11, 2001

(65) Prior Publication Data

US 2002/0158010 A1 Oct. 31, 2002

Related U.S. Application Data

(60) Provisional application No. 60/256,878, filed on Dec. 19, 2000.

(51) Int. Cl.[7] .................................................. C02F 3/00
(52) U.S. Cl. ....................... 210/609; 210/613; 210/764; 210/173
(58) Field of Search ................................ 210/609, 613, 210/764, 173

(56) References Cited

U.S. PATENT DOCUMENTS

| | | | | |
|---|---|---|---|---|
| 4,781,842 A | | 11/1988 | Nicholson | 210/751 |
| 4,849,128 A | * | 7/1989 | Timmons et al. | 252/181 |
| 4,902,431 A | | 2/1990 | Nicholson et al. | 210/751 |
| 5,135,664 A | | 8/1992 | Buraham | 210/751 |
| 5,186,840 A | | 2/1993 | Christy et al. | 210/709 |
| 5,240,599 A | | 8/1993 | Kew et al. | 210/173 |
| 5,275,733 A | | 1/1994 | Burnham | 210/609 |
| 5,282,980 A | | 2/1994 | Kew et al. | 210/787 |
| 5,370,999 A | * | 12/1994 | Stuart | 435/99 |
| 5,409,605 A | | 4/1995 | Haley et al. | 210/199 |
| 5,419,839 A | | 5/1995 | Haley et al. | 210/751 |
| 5,422,015 A | | 6/1995 | Angell et al. | 210/751 |
| 5,482,528 A | | 1/1996 | Angell et al. | 71/12 |
| 5,522,553 A | | 6/1996 | LeClair et al. | 241/21 |
| 5,810,266 A | * | 9/1998 | Nyssen et al. | 24/5 |
| 6,402,065 B1 | * | 6/2002 | Higgins | 241/21 |
| 6,451,281 B1 | * | 9/2002 | Ebeling et al. | 423/640 |

OTHER PUBLICATIONS

Information disclosure statement filed Dec. 11, 2001 describing, "A planner tool comprising: a plurality of vinyl pouch pages; a plurality of lead cards having at least the times of a day; printed calendar sheets having at least a set of days of a week, dates for the days of the week, a plurality of columns with headings, and a duplicate of the times listed on the lead cards".*

Jenkins et al, 1998, "Inactivation of *Cryptosporidium parvum* Oocysts by Ammonia" Applied and Environment Microbiology, p. 784–788.

Leftwich, et al, 1980; "Investigation of Parasites in Southern Domestic Waste Sludge: A Possible Industrial Point Source", Purdue University Industrial Waste Conferece; pp. 910–919.

Carberry et al, 1983, "Sludge Characteristics and Behavior", Martinus Nijhoff Publishers; pp 294–330.

(List continued on next page.)

*Primary Examiner*—Chester T. Barry
(74) *Attorney, Agent, or Firm*—Brown & Michaels, PC

(57) ABSTRACT

A process for destroying pathogens in sludges/biosolids using rotor-stator technology to produce cavitation for pathogen destruction, combined with the feeding of lime or other alkaline material to induce heat and ammonia gas release. The combination of the rotor-stator with the lime produces higher temperatures than the addition of lime alone with a very high mixing efficiency giving maximum pH shift and ammonia release to all portions of the matrix. Overall, the process destroys the resistant stages of helminths or protozoan pathogens through a combination of cavitation with the increased heat caused by the rotor-stator/lime process, along with the locally released ammonia induced by the pH shift.

8 Claims, 3 Drawing Sheets

OTHER PUBLICATIONS

Reimers et al, 1986; "Effectiveness of Wastewater Sludge Treatment Processes to Inactivate Parasites", Wat. Sci Tech. vol. 18, pp 397–404.

Robertson et al, 1992, Survival of *Cryptosporidium parvum* Oocysts under Various Environment Pressures; Applied and Environment Microbiology, pp. 3493–3500.

Ghiglietti et al, 1995, Viability of *Ascaris suum, Acaris Lumbricoides* and *Trichuris M*uris Eggs to Alkaline pH and Different Temperatures, Pa4rassitologia 37: pp 229–232.

Ghiglietti, et al, Survival of *Ascaris Summ* Eggs in Ammonia Treated Wastwater Sludges; Bioresource Technology 59, pp 195–198.

Ruxton, G.D. 1995; Mathematical modelling of ammonia volatilization from slurry stores and its effect on *Cryptosporidium* oocyst viability; Jnl of Agricultural Science; 124, pp 55–60.

Y.A. Chefranova; Jan. 2, 1984; See Summary, p. 41.

Fayer, et al; 1996; Gaseour Disinfection of *Cryptosporidium parvum* Oocysts; Applied and Environmental Microbiology, p. 3908–3909.

Eriksen, et al; 1995; Inactivation of *Ascaris suum* Eggs During Storage in Lime Trea5ed Sewage Sludge; Wat. Res. vol. 30; pp 1026–1029.

* cited by examiner

PATHOGEN INACTIVATION IN BIOSOLIDS WITH CAVITATION

REFERENCE TO RELATED APPLICATIONS

This application claims an invention which was disclosed in Provisional Application No. 60/256,878, filed Dec. 19, 2000, entitled "Pathogen Inactivation in Biosolids with Cavitation." The benefit under 35 USC §119(e) of the United States provisional application is hereby claimed, and the aforementioned application is hereby incorporated herein by reference.

BACKGROUND OF THE INVENTION

1. Field of the Invention

The invention pertains to the field of processing of biosolids. More particularly, the invention pertains to pathogen inactivation in biosolids such as sludge.

2. Description of Related Art

Today, the process of sludge treatment for the purpose of pathogen reduction involves the addition of various high pH materials, such as lime, for pathogen inactivation. The addition of the high pH materials can take place in either the liquid stream or the dry form. Commonly, lime is added to a low speed (e.g. 60 RPM) auger that is mixing dried sludges or just simply added to the sludge. The mixture is then allowed to sit for 12 hours to allow pH and heat to reduce the number of pathogens. However, these processes do not cause a direct physical impact on the pathogens themselves.

Variations on this process have tried to solve the problem of lowering the level of pathogens in sludge. For example, Nicholson's "Method of Treating Wastewater Sludge," U.S. Pat. No. 4,781,842, issued in Nov. 1, 1988; Nicholson et al.'s, "Method for Treating Wastewater Sludge," U.S. Pat. No. 4,902,431, issued Feb. 20, 1990; Burnham's "Process to Stabilize Wastewater Sludge," U.S. Pat. No. 5,275,733, issued on Jan. 4, 1994; Burnham's "Method for Treating Wastewater Sludge," U.S. Pat. No. 5,135,664, issued Aug. 4, 1992; Angell et al's, "Pathogenic Waste Treatment," U.S. Pat. No. 5,482,528, issued Jan. 9, 1995; and Angell et al's, "Pathogenic Waste Treatment," U.S. Pat. No. 5,422,015, issued Jun. 6, 1995 all utilize a pH shift to induce pathogen destruction.

Another example of solutions to lowering the pathogens in sludge is Haley et al's, "Apparatus and Method For Treating Waste Sludge," U.S. Pat. No. 5,419,839, issued May 30, 1995; Christy et al's, "Process for Treating Sewage Sludge," U.S. Pat. No. 5,186,840, issued Feb. 16, 1993; and Haley et al's, "Apparatus and Method for Treating Waste Sludge," U.S. Pat. No. 5,409,605, issued Apr. 25, 1995; all describe mixing chambers that utilize slow augers to add an alkaline substance to cause a pH shaft which will in turn cause pathogen destruction.

The third example of solutions to lowering the pathogens in sludge is Kew et al.'s, "Apparatus for Treatment of Waste Water Sludge," U.S. Pat. No. 5,240,599, issued Aug., 31, 1993; LeClair et al.'s, "Method and Apparatus for Producing Liquid Suspensions of Finely Divided Matter," U.S. Pat. No. 5,522,553, issued Jun. 4, 1996; and Kew et al.'s, "Method for Treatment if Waste Water Sludge," U.S. Pat. No. 5,282, 980, issued Feb. 1, 1994, in these references the rotor/stator has been suggested as a means of treating sludges for the purpose of decreasing particle size and of aiding in dewatering, but it has not previously been considered as a means of either reducing pathogen numbers directly or of being used to introduce lime into the sludge stream as in the present invention.

SUMMARY OF THE INVENTION

The method of pathogen inactivation in biosolids with cavitation using the steps of processing the biosolids in a high-speed rotor/stator mill, digesting the resultant sludge, and adding an alkaline agent to the sludge while it is in a high-speed rotor/stator mill. The resultant treated sludge is then placed in a vessel for at least 12 hours to ensure that the high pH is maintained.

DETAILED DESCRIPTION OF THE INVENTION

The invention is a method of processing biosolids using a high-speed (16,000 RPM) rotor/stator mill for the purpose of producing cavitation in liquid sludges prior to and after digestion.

Figure 1:
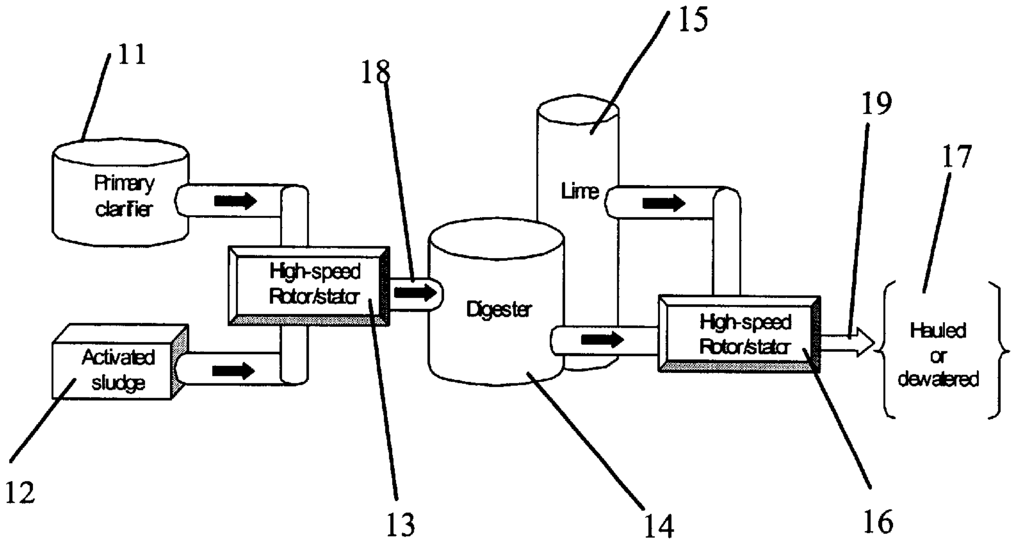
FIG. 1 shows a diagram of one embodiment of an apparatus for use with the method of the invention.

FIG. 1 shows a diagram of an embodiment of a processing apparatus which could be used with the method of the invention. Activated sludge (12) is mixed with a process stream from a primary clarifier (11) in a high-speed rotor-stator mixer (or "mill") (13), such as the Kady rotor-stator mixer manufactured by Kady International of Scarborough, Me., originally developed for mixing paints and the like. This treatment of the liquid waste mixture (18), which consists of a process stream from the primary clarifier (11) and the activated sludge (12) prior to digestion (14), induces cavitation, which causes pathogen lysis or the disruption of internal integrity to the point where the pathogens are inactivated. The output (18) of the mixer (13) is routed into a digestor (14).

The treatment post-digestion (14) involves the addition of an alkaline agent (15) in a high-speed rotor/stator mixer (16), which can be similar to the one (13) used in the primary mixing. The alkaline agent is preferably lime, but could be another alkaline substance such as fly ash or kiln dust or another substance which would result in an adequate pH shift.

The addition of the alkaline agent (15) induces a pH shift to near 12. Heat from the shift in pH and the friction in the rotor/stator assembly is significant in that it further aids the cavitation in the destruction of the pathogens. Furthermore, the pH shift also causes the release of high amounts of ammonia gas. The processing of the mixture in the high-speed rotor-stator mixer (16) ensures that the high levels of ammonia and the high pH are evenly dispersed through out the sludge mixture, resulting in the destruction of all pathogens within the treated biosolids.

An additional step that may prove to be necessary; to comply with EPA guidelines, is to store the treated sludge (19) in a vessel for at least 12 hours to insure that the high pH is maintained in the treated sludge (19). The resulting treated sludge (19) can then be hauled to disposal sites as a liquid, or dewatered prior to hauling by conventional methods (17).

If needed, to control the extent and time of the disruption and mixing, either rotor/stator mixer (13) or rotor/stator mixer (16) can be configured as multiple mixers, connected in series.

Figure 2:
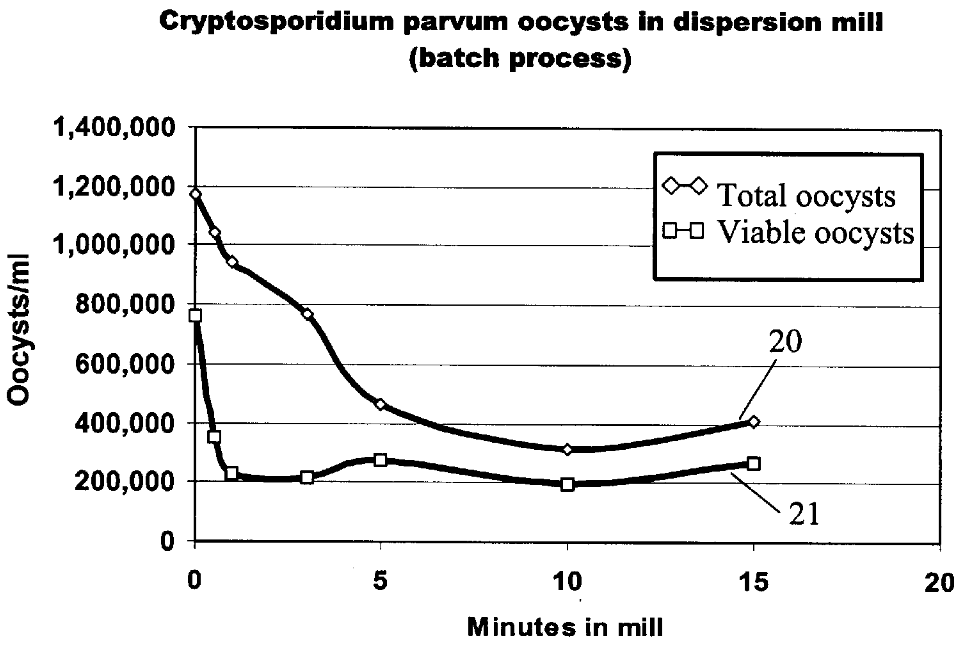
FIG. 2 shows a graph of *C. parvum* oocysts that were viable utilizing the present invention with mill processing.

FIG. 2 shows a graph presenting the results of initial testing using cavitation that would occur in the use of the present invention with a dispersion mill, where the sludge is treated in a batch. Line (20) shows total Oocysts/ml, while line (21) shows viable oocysts/ml. The results show that in water, where heat was removed by an additional system circulating cool water, that there was significant destruction of the oocysts of the protozoan pathogen *Cryptosporidium parvum.*

Figure 3:
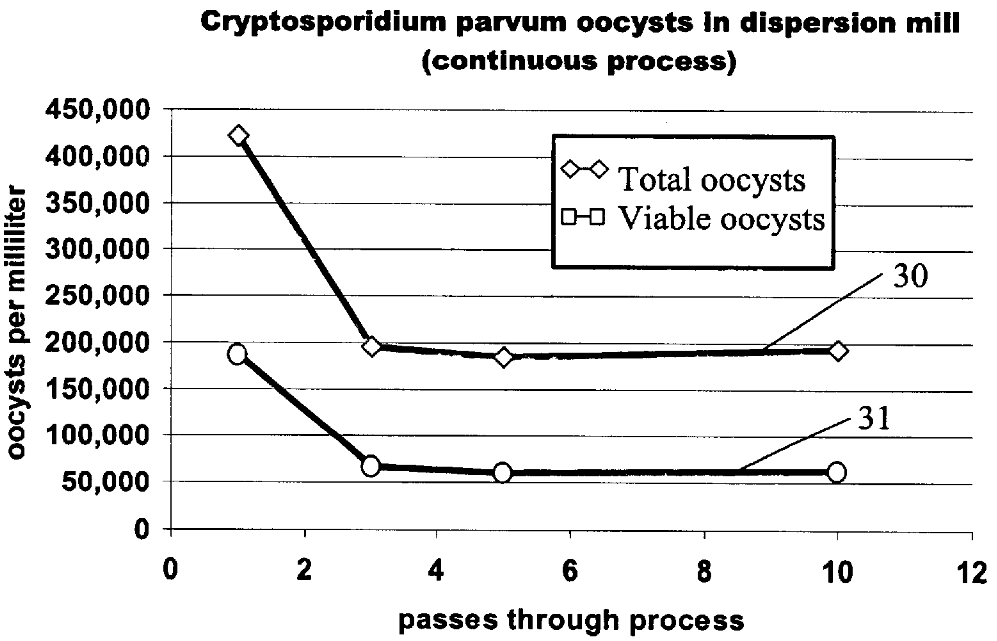
FIG. 3 shows a graph of *C. parvum* oocysts that were viable utilizing the present invention with a continuous line flow.

FIG. 3 shows a graph (30) presenting the results of initial testing using cavitation that would occur in the use of the present invention with a dispersion mill, where the sludge is treated in a continuous flow. Line (30) shows total Oocysts/ml, while line (31) shows viable oocysts/ml. The results show that in water, where heat was removed by an additional system circulating cool water, that there was significant destruction of the oocysts of the protozoan pathogen *Cryptosporidium parvum.*

Figure 4:
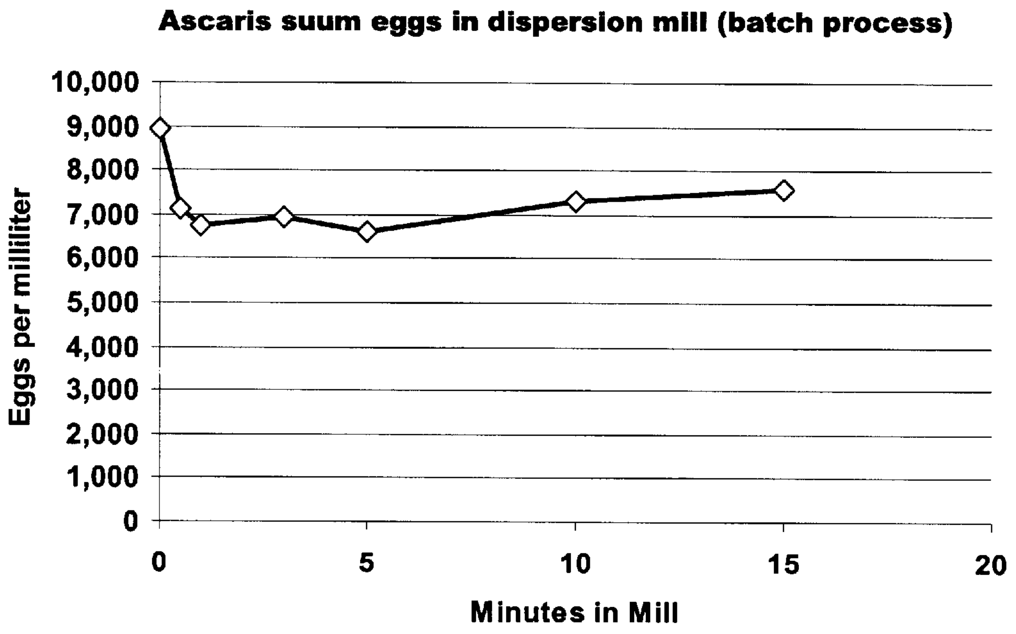
FIG. 4 shows a graph of Ascaris oocysts that were viable utilizing the present invention with mill processing.

FIG. 4 shows a graph presenting the results of initial testing using cavitation that would occur in the use of the present invention with a dispersion mill, where the sludge is treated in a batch. The results show that in water, where heat was removed by an additional system circulating cool water, there was little lysis of the eggs associated with *Ascaris suum*, but did cause the inactivation of the eggs, showing that cavitation is still effective in removing this pathogen.

Figure 5:
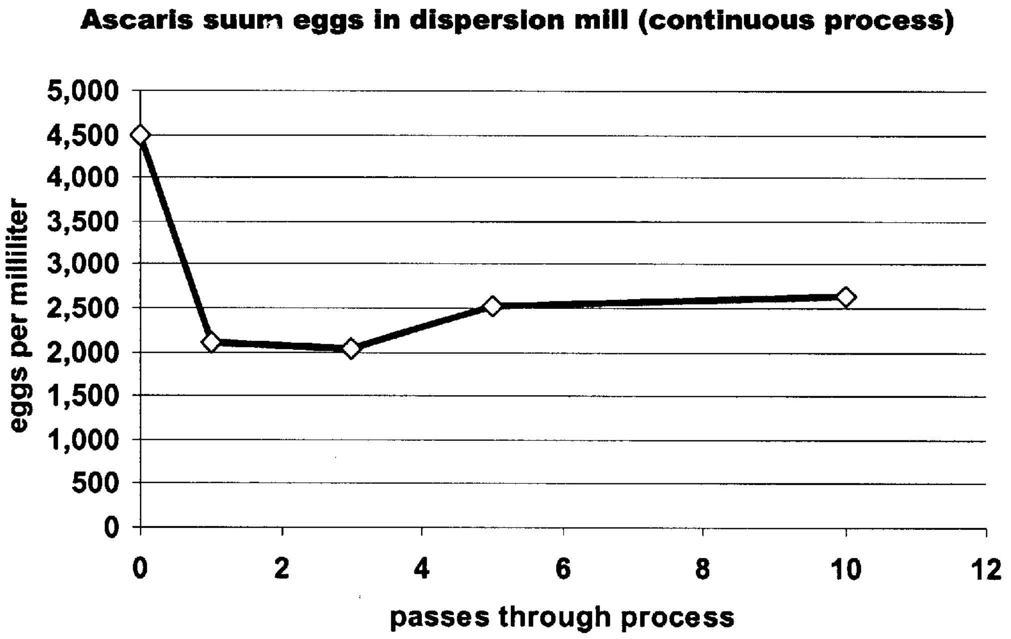
FIG. 5 shows a graph of Ascaris oocysts that were viable utilizing the present invention with a continuous line flow.

FIG. 5 shows a graph presenting the results of initial testing using cavitation that would occur in the use of the present invention with a dispersion mill, where the sludge is treated in a continuous flow. The results show that in water, where heat was removed by an additional system circulating cool water, there was little lysis of the eggs associated with *Ascaris suum*, but did cause the inactivation of the eggs, showing that cavitation is still effective in removing this pathogen.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of pathogen inactivation in biosolids comprising the steps of:

a) digesting the biosolids producing digested biosolids; and b) mixing an alkaline agent with the digested biosolids in at least one high-speed rotor/stator mixer at a speed sufficient to produce cavitation, producing treated sludge.

2. The method of claim 1, further comprising the step, before step (a), of processing the biosolids in at least one high-speed rotor/stator mixer at a speed sufficient to produce cavitation.

3. The method of claim 2, in which the biosolids comprise a mixture of activated sludge and a process stream from a primary clarifier.

4. The method of claim 2, in which the processing step is performed in a plurality of high speed rotor/stator mixers, connected in series.

5. The method of claim 1, further comprising the step of containing the treated sludge in a vessel for at least 12 hours.

6. The method of claim 1, further comprising the step of dewatering the treated sludge.

7. The method of claim 1, in which the mixing step (b) is performed in a plurality of high speed rotor/stator mixers, connected in series.

8. The method of claim 1, wherein the alkaline agent added in step (b) is selected from a group consisting of lime, fly ash, and kiln dust.

* * * * *